US010687993B2

(12) United States Patent
Rudén et al.

(10) Patent No.: US 10,687,993 B2
(45) Date of Patent: Jun. 23, 2020

(54) ABSORBENT ARTICLE WITH INDICATED ABSORPTION ZONE (71) Applicant: ESSITY HYGIENE AND HEALTH AKTIEBOLAG, Göteborg (SE)

(72) Inventors: Marcus Rudén, Göteborg (SE); Stina Lindlöf, Göteborg (SE); Peter Rönnberg, Göteborg (SE)

(73) Assignee: ESSITY HYGIENE AND HEALTH AKTIEBOLAG, Göteborg (SE)

( * ) Notice: Subject to any disclaimer, the term of this patent is extended or adjusted under 35 U.S.C. 154(b) by 0 days.

(21) Appl. No.: 16/098,271

(22) PCT Filed: May 3, 2016

(86) PCT No.: PCT/SE2016/050391
§ 371 (c)(1),
(2) Date: Nov. 1, 2018

(87) PCT Pub. No.: WO2017/192073
PCT Pub. Date: Nov. 9, 2017

(65) Prior Publication Data
US 2019/0117475 A1 Apr. 25, 2019

(51) Int. Cl.
*A61F 13/15* (2006.01)
*A61F 13/513* (2006.01)
(Continued)

(52) U.S. Cl.
CPC .. *A61F 13/51394* (2013.01); *A61F 13/15739* (2013.01); *A61F 13/42* (2013.01);
(Continued)

(58) Field of Classification Search
CPC ...... A61F 13/42; A61F 13/472; A61F 13/475; A61F 13/511; A61F 13/513; A61F 13/514; A61F 2013/4708; A61F 2013/51377
(Continued)

(56) References Cited

U.S. PATENT DOCUMENTS 7,824,385 B2    11/2010  Ecker et al.
2003/0109839 A1  6/2003  Costea et al.
(Continued)

FOREIGN PATENT DOCUMENTS

EP    1 179 329 A1    2/2002
JP    2004-504106 A    2/2004
(Continued)

OTHER PUBLICATIONS

Examination report No. 1 dated Nov. 8, 2018 issued in Australian patent application No. 2016405629.
(Continued)

*Primary Examiner* — Jacqueline F Stephens
(74) *Attorney, Agent, or Firm* — Faegre Drinker Biddle & Reath LLP (57) ABSTRACT

An absorbent hygiene article for placement in underwear is provided, including a liquid permeable topsheet, a backsheet and an absorbent core disposed between the topsheet and the backsheet. The topsheet is of a translucent material and is provided with a colored pattern defining at least one background region and at least one colored region having a first inherent color. The topsheet-facing side of the backsheet has a second color; and a background region located in an inner area has a higher L*-value than a background region located in the edge area.

15 Claims, 2 Drawing Sheets (51) Int. Cl.
*A61F 13/514* (2006.01)
*A61F 13/511* (2006.01)
*A61F 13/47* (2006.01)
*A61F 13/472* (2006.01)
*A61F 13/42* (2006.01)
*A61F 13/475* (2006.01)

(52) U.S. Cl.
CPC .......... *A61F 13/47* (2013.01); *A61F 13/472* (2013.01); *A61F 13/475* (2013.01); *A61F 13/511* (2013.01); *A61F 13/513* (2013.01); *A61F 13/514* (2013.01); *A61F 2013/4708* (2013.01); *A61F 2013/51377* (2013.01)

(58) Field of Classification Search
USPC .................................................. 604/385.01
See application file for complete search history.

(56) References Cited

U.S. PATENT DOCUMENTS

| | | | |
|---|---|---|---|
| 2003/0114811 A1* | 6/2003 | Christon | A61F 13/15203 604/362 |
| 2006/0111684 A1 | 5/2006 | Berba et al. | |
| 2007/0026209 A1 | 2/2007 | MacDonald et al. | |
| 2009/0030391 A1 | 1/2009 | Hammons et al. | |
| 2010/0036351 A1* | 2/2010 | Larson | A61F 13/15203 604/385.01 |
| 2011/0028929 A1 | 2/2011 | Hopkins et al. | |
| 2011/0270208 A1 | 11/2011 | Miura et al. | |
| 2013/0053809 A1 | 2/2013 | Hood et al. | |
| 2013/0261584 A1 | 10/2013 | Lee et al. | |
| 2013/0310784 A1* | 11/2013 | Bryant | A61F 13/51394 604/385.01 |
| 2013/0338621 A1* | 12/2013 | Ecker | A61F 13/472 604/385.01 |
| 2016/0051419 A1 | 2/2016 | Wasson et al. | |

FOREIGN PATENT DOCUMENTS

| | | |
|---|---|---|
| JP | 2006-158538 A | 6/2006 |
| JP | 2007-260411 A | 10/2007 |
| JP | 2010-527682 A | 8/2010 |
| JP | 2011-130798 A | 7/2011 |
| RU | 2232605 C2 | 7/2004 |
| RU | 2411929 C1 | 2/2011 |
| WO | WO-00/35503 A1 | 6/2000 |
| WO | WO-02/07662 A1 | 1/2002 |
| WO | WO-2012/074512 A1 | 6/2012 |
| WO | WO-2016/073694 A1 | 5/2016 |

OTHER PUBLICATIONS

Russian Decision to Grant dated Mar. 28, 2019 issued in Russian patent application No. 2018142128 (10 pages) and its English-language translation thereof (8 pages).
Extended European search report dated Nov. 7, 2019 issued in European patent application No. 16901115.2.
Japanese Notice of Allowance dated Dec. 2, 2019 issued in Japanese patent application No. 2018-558226 (3 pages) and its English-language translation thereof (3 pages).

* cited by examiner

ABSORBENT ARTICLE WITH INDICATED ABSORPTION ZONE

CROSS-REFERENCE TO PRIOR APPLICATION

This application is a § 371 National Stage Application of PCT International Application No. PCT/SE2016/050391 filed May 3, 2016, which is incorporated herein in its entirety.

TECHNICAL FIELD

The present disclosure relates to an absorbent article and to a process for the production of such absorbent article.

BACKGROUND

Absorbent hygiene articles for placement in underwear are well known and may for example be used by persons suffering from incontinence or females during menstruation.

Further, it has become common in the art to provide a printed pattern visible from the topsheet side of such articles to highlight an absorption zone of the article, in order to guide the wearer to a correct placement of the article, as well as providing the wearer with increased confidence in the absorbing capacity of the article.

One approach of providing such printed pattern is disclosed in US2013/0053809.

The printed pattern in US2013/0053809 is synchronized with the extension of the absorbent article, such that it is fairly identically placed on any two articles, both longitudinally and transversely. However, the equipment necessary for positioning a printed pattern in exact position, both longitudinally and transversely, on an absorbing article during a high speed manufacturing process is fairly expensive.

There is consequently a need in the art to be able to indicate an absorption zone without resorting to printing equipment that is capable of providing print that is exact in location, both in longitudinal and transversal direction.

SUMMARY

Disclosed is an absorbent hygiene article for placement in underwear, having a longitudinal extension X and a transversal extension Y when in a flattened out configuration.

The article includes a liquid permeable topsheet, a backsheet and an absorbent core disposed between the topsheet and the backsheet The absorbent core has a core perimeter encircling the core in the X-Y-plane; and an article perimeter encircling the article in the X-Y plane. The article perimeter does not intersect with the absorbent core perimeter.

Further, the article has an edge area defined as the area outside of the absorbent core perimeter and inside of the article perimeter and an inner area inside of the absorbent core perimeter.

The topsheet and said backsheet are joined together in the edge area.

The topsheet is of a translucent material and is provided with a colored pattern defining at least one background region and at least one colored region having a first inherent color. Further, part of the colored regions having said first inherent color is located in the inner area, and part of the colored regions having said first inherent color is located in the edge area. Part of the background region is located in the inner area, and part of the background region is located in the edge area.

The topsheet-facing side of the backsheet has a second color; and the background region located in the inner area has a higher $L^*$-value than the background region located in the edge area.

The present inventors have found that in an absorbent article according to the present disclosure, the portions of the colored pattern that are located in the edge area of the article are less distinguishable from the corresponding background region of the edge area, than are the portions of the colored pattern located in the inner area from the corresponding background regions of the inner area.

Hence, in an article of the present disclosure, the printed pattern has a tendency to disappear in the edge area. In this manner, the inner area of the article, which constitutes the absorbing area, is more clearly indicated.

Disclosed is further a method for producing such absorbent hygiene articles.

BRIEF DESCRIPTION OF THE DRAWINGS

FIG. 1b shows a cross section of the absorbent article in FIG. 1a.

DETAILED DESCRIPTION OF PARTICULAR EMBODIMENTS

Figure 1A:
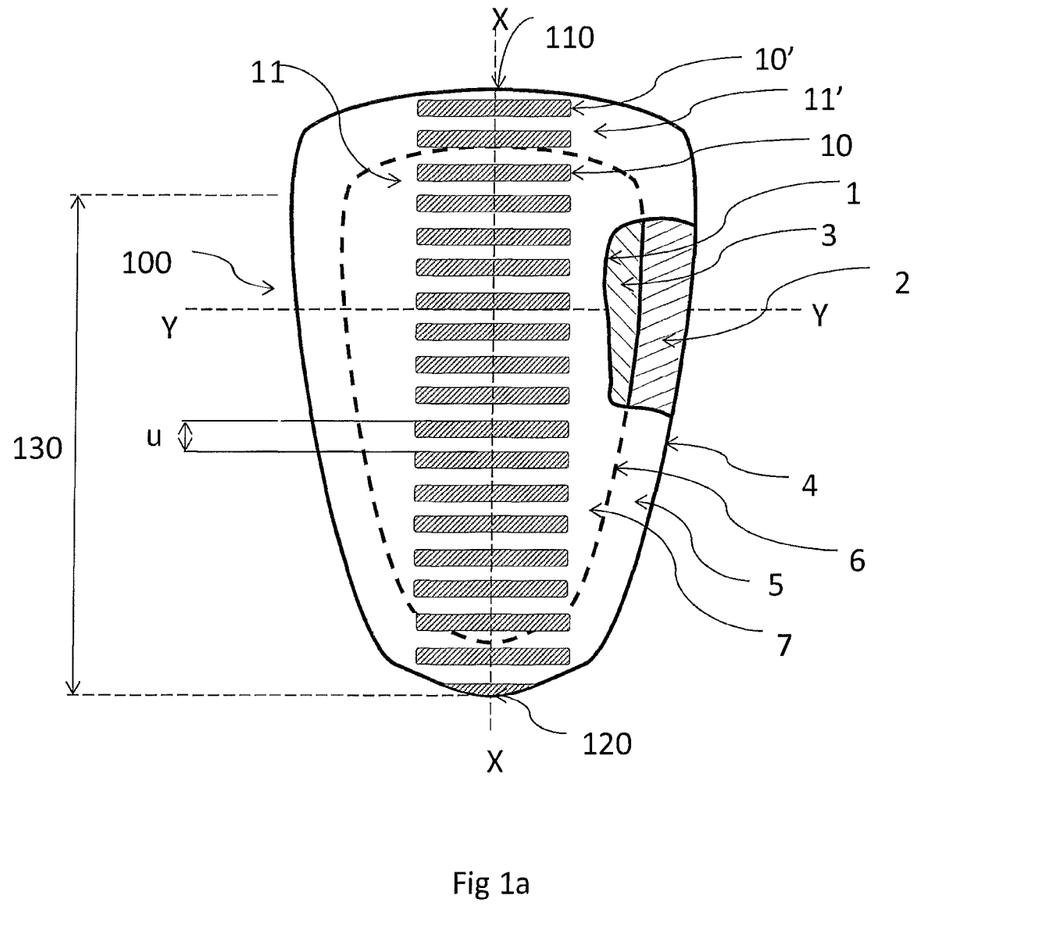
FIG. 1a shows a top view of an absorbent hygiene article.
Figure 1B:
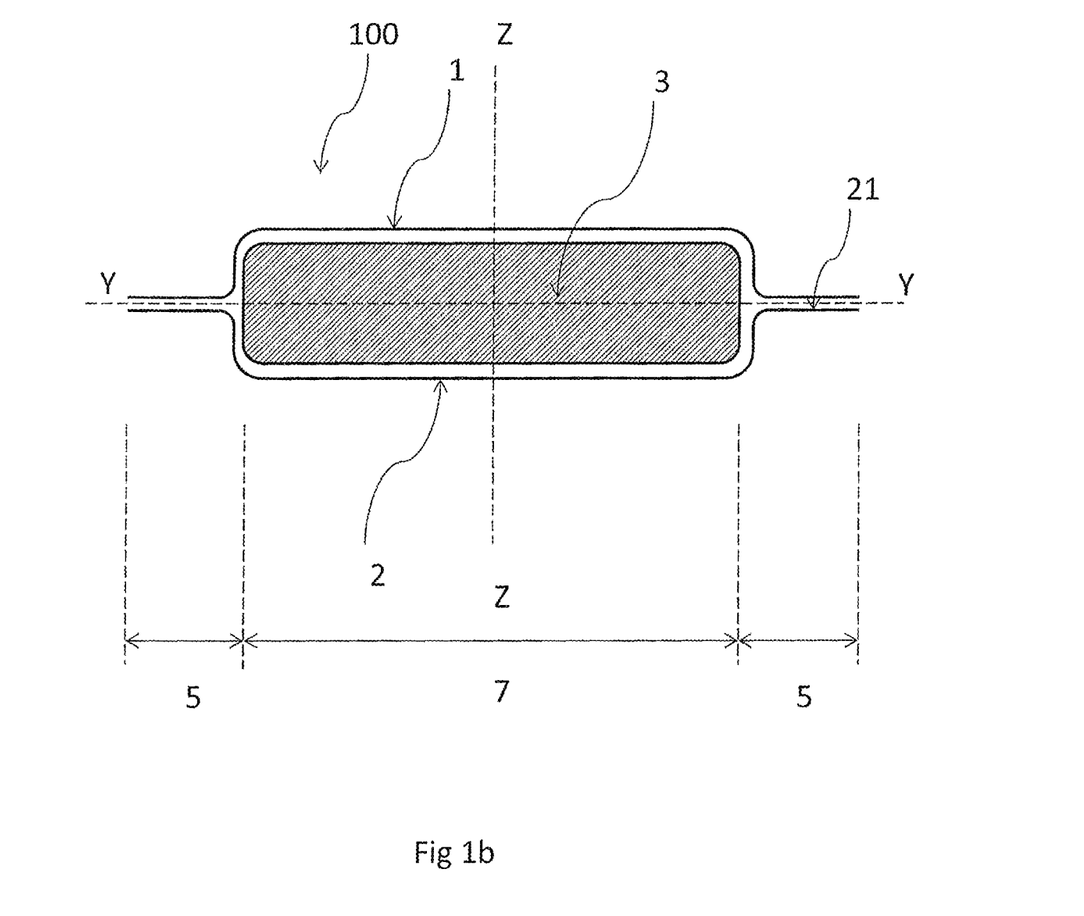

A top view of an absorbent hygiene article 100 in substantially planar configuration is shown in FIG. 1a, and a cross-sectional view of the same is shown in FIG. 1b.

The absorbent hygiene article includes a topsheet 1 and a backsheet 2 and an absorbent core 3 disposed between the top sheet and the backsheet.

The absorbent hygiene article is adapted to be worn such that the topsheet 1 faces the wearer, such that a liquid discharge, such menstrual fluid or urine, is received by the topsheet 1 and thereafter absorbed by the absorbent core 3.

"Absorbent hygiene articles", as referred to herein, can be sanitary napkins, panty liners or incontinence pads that are worn in the crotch region of an undergarment to collect and absorb fluids discharged from the wearer, such as urine or menstrual fluids. The absorbent hygiene articles may be disposable absorbent articles, which are intended to be discarded after a single use, or may be reusable absorbent articles. The absorbent hygiene article may be an incontinence pad especially adapted to be worn by women, by men, or may be gender neutral.

The absorbent hygiene article 100 has a longitudinal extension X and a transversal direction Y, and a thickness extension Z when in a flattened out configuration.

The absorbent hygiene article has a perimeter 4, hereinafter the "article perimeter" which encircles the article in the X-Y plane. The absorbent core 3, disposed between the topsheet 1 and the backsheet 2, has a perimeter 6, hereinafter "the core perimeter" which encircles the absorbent core in the X-Y plane.

The core perimeter 6 is inside of and does not intersect with the article perimeter 4.

The area between the article perimeter and the core perimeter, i.e. the area inside of the article perimeter and outside of the core perimeter, is herein referred to as the edge area 5.

The area inside the core perimeter is hereinafter referred to as the inner area 7.

In embodiments, the minimum width of the edge area at any point around the core perimeter, and taken as the shortest distance in the X-Y-plane of the article from the core perimeter to the article perimeter, is not below 2, such as not below 3, for example not below 5 mm, and/or the maximum width of the edge area at any point of the core perimeter, and taken as the shortest distance in the X-Y-plane of the article from the core perimeter to the article perimeter, is not above 40, such as not above 25, for example not above 15 mm, at any point of the core perimeter.

The topsheet 1 and the backsheet 2 are joined together in the edge area, for example by gluing, by welding, such as by means of ultrasound or a laser, by mechanical joining, such as in the form of embossing or compression, etc., or by some other appropriate method of joining, such as by thermal bonding.

An absorbent hygiene article according to the present disclosure may be designed to be worn in a specific orientation by the wearer. Such absorbent hygiene articles has, along the longitudinal extension, a front end adapted to be located closer to the belly region of the wearer and a rear end, adapted to be located closer to the back region of the wearer.

Absorbent hygiene articles according to the present disclosure may have different shapes, depending on the intended use and intended user, as is conventional in the art. In the context of the present disclosure, "shape" relates to the outer contour of the article in the X-Y plane. The article may have a generally oblong shape as is common for sanitary napkins, being essentially symmetrical in relation to a transverse centerline of the article, or may be asymmetrical in relation to a transverse centerline of the article. The absorbent article may have wing portions along part of longitudinal side edges.

The article may alternatively have a generally triangular, tapered shape, with a wider front region and a narrower rear region, as is shown in FIG. 1a. For example, the absorbent article 100 may have a front end 110 and a rear end 120 mutually opposite of each other along the longitudinal extension of the article, and a central region 130 positioned between the front end and the rear end, which central region constitutes at least 60, such as at least 70, for example at least 80, or at least 90% of the longitudinal extension of the article, and within said central region, the width of the article in the transversal extension gradually increases with the longitudinal distance from the back end.

The topsheet 1 is made of a liquid pervious material to allow passage of liquids there through to the absorbent core 3. The topsheet is further made of a translucent material.

Because the liquid-permeable topsheet 1 is intended to be in direct contact with the user's body, in particular embodiments, the topsheet is manufactured from a material that exhibits characteristics such as dryness and softness when the absorbent product is being worn. It is also desirable for the topsheet to be non-irritating to the skin and to have a soft and textile-like surface which remains dry, even in the event of repeated wetting. The topsheet could consist of, or include, a nonwoven material, e.g. a spunbond nonwoven material, a carded nonwoven material, a thru-air nonwoven material, a spunlace nonwoven (hydroentangled) material, a meltblown nonwoven material, a wetlaid nonwoven material, or a combination of these. Said nonwoven material could be based on either natural fibres such as cellulose or cotton, or alternatively on synthetic fibres such as for example polypropylene (PP), polyethylene (PE) polyester (PET), polyamide (PA), or a combination of these. If a combination is used, this could be a mixture of fibres from different natural and/or synthetic polymers, although each fibre can also contain different polymers (for example PP/PE bi-component fibres or PP/PE copolymers).

The topsheet may consist of, or include, a perforated, hydrophobic nonwoven material in order to keep the surface which is closest to the user's body dry. Additionally, the holes of the perforated, hydrophobic nonwoven material may impart a textile-like and comfortable feel to the topsheet.

The topsheet may further consist of, or include, a perforated plastic film. The diameter of the holes of such a perforated, hydrophobic nonwoven material is larger than the distance between the fibers in the material. In this way, liquid can be led down through the holes in the topsheet to the subjacent absorbent core.

The liquid-permeable topsheet could also include several layers of material, i.e. a laminate. Such a laminate could for example include a first and a second layer of materials. Alternatively, the laminate could consist of the same material or a combination of the following materials: perforated film/nonwoven, perforated film/perforated film, nonwoven/nonwoven, perforated nonwoven/nonwoven, and perforated nonwoven/perforated nonwoven.

The topsheet may be made from renewable raw materials.

The absorbent core 3 is the absorbent structure between the topsheet 1 and the backsheet 2 of the absorbent hygiene article 100. The absorbent core 3 could be of any conventional kind. Examples of commonly occurring absorbent materials are cellulosic fluff pulp, tissue layers, highly absorbent polymers, so-called super absorbent polymers (SAP), absorbent foam materials, absorbent non-wovens or the like. Organic materials suitable for use as super absorbent materials include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. In particular embodiments, the hydrogel polymers are lightly crosslinked to render the material substantially water insoluble. In particular embodiments, super absorbent materials are further surface crosslinked so that the outer surface or shell of the super absorbent particle, fiber, flake, sphere, etc. possesses a higher crosslink density than the inner portion of the super absorbent. The super absorbent materials may be in any form suitable for use in absorbent composites including particles, fibers, flakes, spheres, and the like.

It is common to combine cellulosic fluff pulp with super absorbents in an absorbent core. It is also conventional to have absorbent cores including layers of different materials with different properties in terms of liquid acquisition capacity, liquid distribution capacity and storage capacity.

The backsheet 2 may be of any material commonly used in the art for that purpose. The backsheet may be at least essentially, or completely liquid impervious.

The backsheet may consist of a plastic film, e.g. a polyethylene or polypropylene film, a non-woven material which for example could be treated with a liquid impervious material or a hydrophobic non-woven material which resists liquid penetration, or a laminate including plastic films and nonwoven materials. Other types of liquid barrier materials could also be used as liquid-impermeable backsheets, such as e.g. closed-cell plastic foams or various liquid barrier laminates. In particular embodiments, the backsheet is permeable to air and vapor so as to allow vapor to escape from the absorbent core, while still preventing liquids from passing there through. Examples of breathable backsheet materials are porous polymeric films, nonwoven laminates from spunbond and meltblown layers, laminates from porous polymeric films and nonwovens.

Another suitable design of the backsheet is to use a laminate with a textile nonwoven outer layer having a tailored appearance to the absorbent hygiene article such that there is a soft and non-sticky portion where the backsheet may come into contact with the user's skin.

"Color", as referred to herein includes any primary color, i.e. white, black, red, blue, violet, orange, yellow, green and indigo, as well as any declination thereof or mixture thereof.

In the context of the present disclosure, colors, such as the color of the background region(s) and the colored region(s) are measured by a reflectance spectrophotometer according to the colors' L*, a* and b* values.

The L*, a*, and b* values of the absorbent hygiene articles are measured from the body facing surface 10 of the article 5 inboard of the article perimeter. The inherent L*, a*, and b* values of a component of the absorbent hygiene articles, such as of the topsheet or the backsheet, are measured from the indicated surface of that material inboard of the perimeter of such material.

The difference in color is calculated using the L*, a*, and b* values by the equation:

$$\Delta E = [(L^*_X - L^*_Y)^2 + (a^*_X - a^*_Y)^2 + (b^*_X - b^*_Y)^2]^{1/2} \quad (I)$$

The 'X' in equation (I) represents a first measuring point, and may for example represent a background region located in the inner area of the article, a background region located in the edge area of the article, a background region of the top-sheet material per se, etc, and 'Y' may represent the color of second region against which the color of the first region is compared. X and Y should not be the same two points of measurement at the same time. Where more than two colors are used, the 'X' and 'Y' values alternately include points of measurement in them also. The key to the ΔE calculation herein is that the 'X' and 'Y' values should not stem from the same measured point on the viewing surface.

In the context of the present specification, color, i.e. L*, a* and b* values, were measured using a Techkon SpetroDens Premium measurement device obtainable from Techkon of Danvers, Mass., US.

Measurements were performed at an ambient temperature of between 23±1° C. and a relative humidity of 50±10%. The measured article was acclimatized at these measurement conditions for at least 24 h prior to measurement.

The spectrophotometer was set to the CIELab color scale and settings D50/2°/noPOL/ABS, according to the User's manual, and equipped with a 1.5 mm or 3 mm aperture.

Either the 3 or 1.5 mm aperture may be used, as long as all measurements to be compared with each other are made using the same aperture. The aperture can be chosen such that the region, in which the color is to be measured, is larger than the aperture.

In the measurements reported in the present disclosure, a 1.5 mm aperture was used.

The spectrophotometer is calibrated prior to sample analysis utilizing the white reference tiles supplied from the vendor with the instrument. Calibration is done according to the manufacturer's instructions as set forth in User's manual. Any sample point on the absorbent article containing the imparted color to be analyzed can be selected.

The object of measurement is placed on top of a stack of three sheets of white standard office printing paper (Everyday paper 80 g/m³ from Office Depot, Sweden), which in turn is placed on a bench of white, opaque material. The L*-value measured on the top of the stack was 96±1.

The object of measurement is to be in a substantially flat condition and free of wrinkles.

For each reported value, ten (10) readings of color are conducted at different locations. If possible (e.g., the size of the imparted color on the element in question does not limit the ability to have ten discretely different, non-overlapping sample points), each of the readings is to be performed at a substantially different region so that no two sample points overlap. If the size of the imparted colored region requires overlapping of sample points, the samples should be taken with the sample points selected to minimize overlap between any two sample points. The readings are averaged to yield the reported L*, a*, and b* values for a specified color.

It is foreseen that any equipment suitable to measure L*, a* and b* values according to the CIELab color scale on the type of material used in absorbent hygiene articles could be used to obtain the values disclosed in the present application.

In the context of the present disclosure, a difference is made between an inherent color (L* or a* or b* value) of a material and the color in the assembled absorbent hygiene article. An inherent color is measured on the material per se, while the corresponding value for the absorbent hygiene article is measured on the assembled article. Unless a color is indicated to represent the inherent color, it is to be understood that the value is measured on the assembled absorbent hygiene article.

It is to be understood in the context of the present disclosure are performed according to the color measurement method disclosed herein.

The topsheet is made of a translucent material, i.e. it permits light to pass through. The topsheet material may have an inherent L*-value that is at least 80, such as at least 85, for example at least 90, and at most 96.

The topsheet is provided with a printed pattern, which defines at least one background region (11) and at least one colored region (10) having a first inherent color. In the background region(s), no print is applied.

In the context of the present disclosure, a colored region having a specific color, such as a colored region having a first inherent color, is a region within the boundaries of which the specific color is substantially homogenous.

The article 100 is assembled such that part of the printed pattern 10 is located in the inner area 7 of the absorbent hygiene article and part of the printed pattern 10' is located in the edge area 5 of the absorbent hygiene article. In the context of the present disclosure, this allows for one continuous colored region having the first inherent color to extend from the inner area to the edge area, and/or for a first colored region 10 having the first inherent color to be located solely in the inner area and a second colored region 10' having the first inherent color, to be located solely in the edge area.

Further, the article 100 is assembled such that part of the background region(s) 11 is located in the inner area 7 of the absorbent hygiene article and part of the background region(s) 11' is located in the edge area 5 of the absorbent hygiene article. In the context of the present disclosure, this allows for one continuous background region to extend from the inner area to the edge area, and/or for a first background region to be located solely in the inner area and a second background region to be located solely in the edge area.

The printed pattern may provide a single, continuous, colored region and a plurality of background regions, i.e. with the background regions representing discrete islands in a continuous colored region, or may provide a plurality of colored regions and a single, continuous, background region, i.e. with the printed regions representing discrete islands in a continuous background region, as is illustrated in FIG. 1a, or may provide a plurality of colored regions and a plurality of background regions. When the printed pattern provides a plurality of printed regions, each one may having substantially the same color, or optionally the pattern may comprise different colored regions with different inherent colors, as long as the absorbent hygiene article is assembled such that there is at least one colored region with a first inherent color that extends from the inner area to the edge are of the article, or such that there is at least a first colored region having the first inherent color in the inner area of the article, and at least second colored region having the first inherent color in the edge area of the article.

In the context of the present disclosure, two colored regions are deemed having the same color if the $\Delta E$ between the two regions is below 2, or below 1.

The colored region(s) may cover from 1, such as from 2, for example from 5, to 90, such as to 50, for example to 20 area %, based on the total area of the topsheet.

The colored region(s) may cover from 1, such as from 2, for example from 5, to 90, such as to 50, for example to 20 area %, based on the edge area.

The colored region(s) may cover from 1, such as from 2, for example from 5, to 90, such as to 50, for example to 20 area %, based on the central area.

The ratio of the area percentage of the edge area covered by the colored regions to the area percentage of the inner area covered by the colored regions may be from 10:1 to 1:10, such as from 5:1 to 1:5, for example from 2:1 to 1:2.

The backsheet may be translucent or may be opaque. At least the side of the backsheet that faces the topsheet is provided with a color having an inherent $L^*$-value that is significantly lower than the inherent $L^*$-value of the topsheet, and lower than the inherent $L^*$-value of topsheet facing surface of the absorbent core.

As the topsheet material is translucent, the consequence is that the background region 11 located in the inner area 7 of the absorbent hygiene article obtains a higher $L^*$-value than the background region 11' located in the edge area 5.

The color on the topsheet-facing side of the backsheet may be substantially uniform, at least within the area of the backsheet that will be part of the edge area of the absorbent hygiene article when assembled.

In the context of the present disclosure, an area having "substantially uniform color" is to be interpreted as the color difference ($\Delta E$) between any two regions of the same area is at most 2, or at most 1.

Alternatively, the color on the topsheet-facing side of the backsheet may vary over the surface, so long as that portion of the topsheet-facing side of the backsheet that has the highest inherent $L^*$-value, has an inherent $L^*$-value that is lower than the inherent $L^*$-value of the topsheet facing side of the absorbent core.

The color may be applied to the backsheet in any manner known to the person skilled in the art, resulting in the desired color. For example, the backsheet may be of, or comprise, a material having an inherent color, or may be subjected to a print process to provide the backsheet color. In some embodiments, the backsheet comprises, or consist of, a plastic film, which may be made from a pigmented plastic material.

Due to the translucency of the topsheet, the side of the backsheet that faces the topsheet, will at least partly be visible through the translucent topsheet and therefore make the background regions in the edge area to appear darker.

The absorbent core and/or other layers located between the absorbent core and the topsheet are selected such that the background region(s) located the inner area have a higher $L^*$-value, i.e. appear brighter, than the background region(s) located in the edge area.

In embodiments of the absorbent hygiene article, the $L^*$-value of the background region 11 located in the inner area 7 of the absorbent hygiene article is at least 75, at least 78, at least 80, at least 83, at least 87 or at least 90, and is at most 100 or at most 95.

The difference between $L^*$-value of the background region 11 located in the inner area (7) and the $L^*$-value of the background region 11' located in the edge area (5), hereinafter "$\Delta L^*_{background}$" may be up to 100% of the $L^*$-value of the background region 11 located in the inner area (7), given that the lowest possible $L^*$-value of the background region 11' located in the edge area (5) is 0. However in embodiments of the absorbent hygiene article, $\Delta L^*_{background}$ may be from at least 5, at least 7, at least 10, or at least 20, and at most 80, such as at most 60, for example at most 50.

In embodiments of the absorbent hygiene article, the color difference between the colored region 10 located in the inner area 7 and the background region 11 located in the inner area, hereinafter "$\Delta E_{inner}$", of the absorbent hygiene article is higher than the color difference between the colored region 10' located in the edge area 5 and the background region 11' located in the edge area, hereinafter "$\Delta E_{edge}$". For example, $\Delta E_{inner}$ may be higher than $\Delta E_{edge}$ ($\Delta E_{inner} - \Delta E_{edge}$) by at least 0.5, at least 1, at least 2, or at least 3, such as at least 5 or even at least 10 units. The upper limit of ($\Delta E_{inner} - \Delta E_{edge}$) is $\Delta E_{inner}$, given that $\Delta E_{edge}$ could be zero. In embodiments of the absorbent hygiene article ($\Delta E_{inner} - \Delta E_{edge}$) is at most 90, 80, 70 or 50% of $\Delta E_{inner}$.

In embodiments of the absorbent hygiene article $\Delta E_{inner}$ may be at least 2, at least 4, at least 8, at least 10. The upper limit of $\Delta E_{inner}$ depends on the color of the background region in the inner area and is at most 100, at most 80, at most 60, or at most 40.

The colored pattern may be applied on the topsheet material by any printing means commonly known in the art, such as by means of non-contact printing, for example ink-jet printing, or contact printing, for example gravure printing, flexographic printing, lithographic printing and screen printing, or by combinations of different printing methods. For example, one part of the colored pattern may be applied by contact printing, and another part of the pattern may be applied by non-contact printing. The pattern may be provided on the surface of said topsheet facing away from said backsheet, or on the surface of said topsheet facing said back sheet, or alternatively, part of the pattern may be provided on the surface of said topsheet facing away from said backsheet while part of the pattern is provided on the surface of said topsheet facing said backsheet.

In embodiments, the colored pattern is repetitive along a printing direction. The printing direction is typically parallel to the machine direction in which the products are produced, and may for example be substantially parallel to the longitudinal or transversal extension of said absorbent article, having a repeating unit length of less than or equal to the maximum length of the absorbent article along said longitudinal extension or transversal extension, respectively.

The length of the repeating unit may for example be in the range of from 1, such as 2, for example 3 cm to 25, such as to 15, for example to 10 cm.

When the colored pattern is repetitive as mentioned hereabove, the observer will readily recognize the repeating unit length by ocular inspection and consequently recognize corresponding components of the printed pattern in different repeating units of the pattern.

When the pattern is repetitive as mentioned hereabove, the background region selected for measuring the color in the edge area the background region selected for measuring the color in the inner area, can be selected to represent the same position in the pattern however belonging to two different repeating units of the pattern. Likewise, the colored region selected for measuring the color in the edge area the colored region selected for measuring the color in the inner area, can be selected to represent the same position in the pattern belonging to two different repeating units of the pattern.

In other words, the corresponding points are separated, along the direction of repetition, by a distance of n*u, where n is a non-zero integer and u is the length of the repeating unit, and, and positioned along a same imaginary line parallel to the direction of repetition.

Alternatively, the colored pattern is not repetitive, or is repetitive in a direction along a longitudinal extension of said absorbent article, having a repeating unit length longer than the maximum length of the absorbent article along said longitudinal extension or, the pattern may be repetitive in a direction along a transverse extension of said absorbent article, having a repeating unit longer than the maximum width of the absorbent article along said longitudinal extension.

In embodiments of the absorbent hygiene article, the color of that surface of the backsheet that faces away from the topsheet, i.e. on the back-side of the article, exhibits a color that is close to that of the aforementioned background region 11' in the edge area 5. For example, that color difference (ΔE) may be below 3, such as below 2, for example below 1.

As will be realized by those skilled in the art, the absorbent hygiene article may comprise further layers or components apart from the topsheet, the absorbent core and the backsheet. Such layers or components include elastic threads, liquid barriers, wetness indicators, fluid acquisition layers, etc.

For example, the absorbent hygiene article may include a fluid acquisition layer for a quick transport of body fluids. The fluid acquisition layer has an open porous structure and should be able to quickly receive and temporarily store a certain amount of fluid and transfer it further to the underlying absorbent core. This is important, especially for thin, compressed absorbent articles of today, which often have a high content of SAP. Although these articles certainly have high absorption capacities, they sometimes have long acquisition times and cannot instantaneously cope with receiving the large amounts of liquid which can be released within a few seconds during urination. The fluid acquisition layer is usually a so-called high loft material and may be produced by carding and through-air bonding or by needling of synthetic fibers, such as polyester, polypropylene or mixtures thereof.

Further, the outer surface of the backsheet, i.e. the surface of the backsheet facing away from the topsheet, may be provided with a fastening means to secure placement of the article in underwear. Such fastening means include, but are not limited to such means commonly known to the person skilled in the art, such as hook material, one or more strips of adhesive, or snap buttons.

Disclosed is also a process for the manufacture of absorbent hygiene articles as defined in this specification. General processes for the manufacture of absorbent hygiene articles suitable for placement in underwear, i.e. absorbent pads, are well known in the art, and generally includes the steps of sandwiching an absorbent core between a top sheet substrate and a backsheet substrate, joining the topsheet substrate to the backsheet substrate and optionally cutting away excess material from the area laterally outside the absorbent core, to obtain the desired article perimeter. By this, such article defines the article perimeter, the core perimeter, the edge area and the inner area as described previously.

In the process of the present disclosure, the topsheet substrate is of a translucent material, and the process further comprises the steps of providing a colored pattern on the top sheet, which pattern defines at least one background, non-printed, region, and at least one colored region of a first inherent color. The topsheet substrate may be provided with the colored pattern at any stage during the product assembly process, or may already be provided to the topsheet substrate prior to and/or separate from the product assembly process.

Further, the topsheet facing surface of the back sheet substrate is a material that has an inherent L*-value that is lower than the inherent L*-value of the background regions of the topsheet substrate.

In the product assembly process, the topsheet substrate and the backsheet substrate are arranged such that at least part of the background region(s) and at least part of the printed region(s) having the first inherent color are present in the edge area of the article, and such that at least part of the background region(s) and at least part of the printed region(s) having the first inherent color are present in the inner area of the article.

EXAMPLES

From four (4) different printed topsheet materials and four (4) different backsheet materials, five (5) different absorbent hygiene products was assembled as indicated below. Absorbent material, a mixture of pulp fibers at 420 g/m$^2$ and SAP particles at 150 g/m$^2$, was sandwiched between the topsheet material and the backsheet material, and in the edge area, the topsheet and backsheet was joined together using standard hot-melt glue.

The topsheet material was spunbond non-woven, 18 g/m$^2$ grammage.

Topsheet A1 was printed with a blue print according to a first pattern.

Topsheet A2 was printed with a blue print according to a second pattern.

Topsheet A3 was printed with a blue print according to a third pattern.

Topsheet B was printed with a grey print

The backsheet material was a laminate of a polyethylene barrier film, 18 g/m$^2$ and a spunbond non-woven, 18 g/m2.

In backsheet material I, the barrier film was pigmented into a blue color.

In backsheet material II, the barrier film was pigmented into a light grey color In backsheet material III, the barrier film was pigmented into a dark grey color.

In backsheet material IV, the barrier film was pigmented into a grey color.

The products were assembled with the PE-film layer of the backsheet material facing the topsheet.

TABLE 1

| Sample | Topsheet | Backsheet |
|---|---|---|
| 1 | A1 | IV |
| 2 | B | I |
| 3 | A2 | II |
| 4 | A3 | I |
| 5 | A4 | III |

Color measurements on the assembled products were performed according to the method described herein:

TABLE 2

Background region, inner area (over absorbent core)

| Sample | L value | a value | b value |
|---|---|---|---|
| 1 | 83.744 | −0.618 | 0.261 |
| 2 | 85.301 | −0.692 | 0.975 |
| 3 | 85.34 | −0.499 | 1.276 |
| 4 | 85.06 | −0.584 | 1.149 |
| 5 | 84.39 | −0.524 | 1.156 |

TABLE 3

Colored region, inner area (over absorbent core)

| Sample | L value | a value | b value |
|---|---|---|---|
| 1 | 76.63 | −2.705 | −6.722 |
| 2 | 81.075 | −1.729 | −1.122 |
| 3 | 76.958 | −1.175 | −0.246 |
| 4 | 77.792 | −2.298 | −2.583 |
| 5 | 74.779 | −1.199 | 0.299 |

TABLE 4

Background region, edge area (outside absorbent core)

| Sample | L value | a value | b value |
|---|---|---|---|
| 1 | 78.901 | −0.496 | −1.457 |
| 2 | 73.773 | −3.365 | −7.973 |
| 3 | 59.573 | 1.166 | 1.497 |
| 4 | 73.473 | −3.401 | −7.81 |
| 5 | 49.681 | 0.129 | 0.234 |

TABLE 5

Colored region, edge area (outside absorbent core)

| Sample | L value | a value | b value |
|---|---|---|---|
| 1 | 73.526 | −2.469 | −7.476 |
| 2 | 70.054 | −4.015 | −8.871 |
| 3 | 56.175 | 0.812 | 0.669 |
| 4 | 68.33 | −4.594 | −9.887 |
| 5 | 40.761 | −0.261 | −0.441 |

TABLE 6

| Sample | $\Delta E_{inner}$ (over abs. core) | $\Delta E_{edge}$ (outside abs. core) | Difference ($\Delta E_{inner} - \Delta E_{edge}$) |
|---|---|---|---|
| 1 | 10.18 | 8.31 | 1.88 |
| 2 | 4.83 | 3.88 | 0.95 |
| 3 | 8.55 | 3.52 | 5.03 |
| 4 | 8.35 | 5.67 | 2.67 |
| 5 | 9.67 | 8.95 | 0.72 |

As is seen from the results above, the color difference between the printed region and the background region is consistently lower in the edge area than in the inner area, meaning that the printed region is less distinguishable from the background region in the edge area compared to in the inner area.

The invention claimed is:

1. An absorbent hygiene article for placement in underwear having a longitudinal extension X and a transversal extension Y when in a flattened out configuration, said article comprising:
    a liquid permeable topsheet; a backsheet; and an absorbent core disposed between the topsheet and the backsheet forming an assembled article, said absorbent core having a core perimeter encircling the core in the X-Y-plane;
    said article further having an article perimeter encircling the article in the X-Y plane, which article perimeter does not intersect with the absorbent core perimeter;
    an edge area defined as the area outside of the absorbent core perimeter and inside of the article perimeter; and
    an inner area inside of the absorbent core perimeter, wherein:
        said topsheet and said backsheet are joined together in the edge area;
        said topsheet is of a translucent material and is provided with a colored pattern defining at least one background region having a background inherent color and at least one colored region having a first inherent color;
        a first part of the colored regions having said first inherent color is located in the inner area and a second part of the colored regions having said first inherent color is located in the edge area;
        a first part of the background region having said background inherent color is located in the inner area and a second part of the background region having said background inherent color is located in the edge area;
        the topsheet-facing side of the backsheet has a second inherent color; and
        the first part of the background region has a color in the assembled article located in the inner area having a higher L*-value than a color in the assembled article of the second part of the background region located in the edge area, wherein the inherent color relates to color value measured on the topsheet or backsheet separately and the color in the assembled article relates to color value measured on the topsheet of the hygiene absorbent article as assembled.

2. The absorbent hygiene article according to claim 1, wherein the L*-value of the first part of the background region located in the inner area is at least 5 units higher than the L* value of the second part of the background region located in the edge area.

3. The absorbent hygiene article according to claim 1, wherein the color difference between the inherent color of said colored region and the inherent color of said background region (ΔEinherent) is at least 2.

4. The absorbent hygiene article according to claim 1, wherein the color difference between the first part of said colored region located in the inner area and the first part of the background region located in the inner area is higher than the color difference between the second part of the said colored region located in the edge area and the second part of the background region located in the edge area (ΔEedge).

5. The absorbent hygiene article according to claim 4, wherein ΔEinner is at least 2.

6. The absorbent hygiene article according to claim 4, wherein ΔEinner−ΔEedge is at least 2.

7. The absorbent hygiene article according to claim 1, wherein the L*-value of the first part of the background region located in the inner area is at least 75.

8. The absorbent hygiene article according to claim 1, wherein the colored regions cover from 1 to 90 area %, based on the total area of the topsheet; and/or
wherein the second part of the colored regions located in the edge area cover from 1 to 90 area %, based on the edge area; and/or
wherein the first part of the colored regions located in the inner area cover from 1 to 90 area %, based on inner area.

9. The absorbent hygiene article according to claim 1, wherein the ratio of the area percentage of the edge area covered by the second part of the colored regions to the area percentage of the inner area covered by the first part of the colored regions is from 10:1 to 1:10.

10. The absorbent article according to claim 1, wherein the background region is one continuous region and the colored regions are a plurality of regions, or
background regions are a plurality of regions and the colored region is one continuous region, or
the background regions are a plurality regions and the colored regions are a plurality regions.

11. The absorbent hygiene article according to claim 1, wherein said colored pattern is repetitive in a direction along a longitudinal extension of said absorbent article, having a repeating unit length of less than or equal to the length of the absorbent article along said longitudinal extension; or said pattern is repetitive in a direction along a transverse extension of said absorbent article, having a repeating unit length of less than or equal to the width of the absorbent article along said longitudinal extension.

12. The absorbent article according to claim 1, wherein the absorbent article is an incontinence pad or a panty liner.

13. The absorbent article according to claim 1, having a front end and a rear end arranged mutually opposite of each other along the longitudinal extension of the article, and a central region positioned between the front end and the rear end, which central region constitutes at least 50% of the longitudinal extension of the article, and wherein the width of the article in the transversal extension gradually increases with the longitudinal distance from the back end within said central region.

14. A process for the production of an absorbent article, comprising:
providing a translucent liquid-permeable top sheet substrate;
providing an absorbent core;
providing a backsheet substrate;
arranging said absorbent core between said topsheet and backsheet substrates, such that the perimeter of the absorbent core is located inside the perimeter of the top sheet and back sheet substrates, respectively; and
joining said first and second substrates in an area outside the perimeter of the absorbent core to form an assembled article;
providing said topsheet substrate with a colored pattern defining at least one background region having a background inherent color and at least one colored region having a first inherent color;
providing the topsheet facing surface of the backsheet substrate with a second inherent color; and
aligning said topsheet and backsheet substrates such that a first part of the colored regions having said first inherent color is located in the inner area, a second part of the colored regions having said first inherent color are located in the edge area, a first part of the background region is located in the inner area, and a second part of the background region is located in the edge area,
wherein the first part of the background region having said background inherent color and located in the inner area has a color in the assembled article having a higher L*-value than a color in the assembled article of the second part of the background region having said background inherent color and located in the edge area, wherein the inherent color relates to color value measured on the topsheet or backsheet separately and the color in the assembled article relates to color value measured on the topsheet of the hygiene absorbent article as assembled.

15. A method according to claim 14, wherein topsheet substrate is provided with said colored pattern prior to the step of arranging an absorbent core between the topsheet substrate and the backsheet substrate.

* * * * *